United States Patent
Goyal et al.

(10) Patent No.: US 12,011,224 B2
(45) Date of Patent: Jun. 18, 2024

(54) METHOD FOR DETERMINING REFRACTIVE POWER OF EYE USING IMMERSIVE SYSTEM AND ELECTRONIC DEVICE THEREOF

(71) Applicant: Samsung Electronics Co., Ltd., Suwon-si (KR)

(72) Inventors: Ashish Goyal, Bangalore (IN); Vijay Narayan Tiwari, Bangalore (IN); Tushar Sircar, Bangalore (IN); Aloknath De, Bangalore (IN)

(73) Assignee: Samsung Electronics Co., Ltd., Suwon-si (KR)

( * ) Notice: Subject to any disclaimer, the term of this patent is extended or adjusted under 35 U.S.C. 154(b) by 895 days.

(21) Appl. No.: 16/967,948

(22) PCT Filed: Feb. 7, 2019

(86) PCT No.: PCT/KR2019/001539
§ 371 (c)(1),
(2) Date: Aug. 6, 2020

(87) PCT Pub. No.: WO2019/156485
PCT Pub. Date: Aug. 15, 2019

(65) Prior Publication Data
US 2021/0030270 A1 Feb. 4, 2021

(30) Foreign Application Priority Data

Feb. 7, 2018 (IN) .............................. 201841004682
Feb. 4, 2019 (IN) ........................... 2018 41004682

(51) Int. Cl.
*A61B 3/103* (2006.01)
*G02B 27/01* (2006.01)
(Continued)

(52) U.S. Cl.
CPC .......... *A61B 3/103* (2013.01); *G02B 27/0172* (2013.01); *G06V 40/161* (2022.01); *G06V 40/18* (2022.01)

(58) Field of Classification Search
CPC ........... A61B 3/103; A61B 3/10; A61B 3/107; A61B 3/1035; A61B 3/18; G06V 40/18;
(Continued)

(56) References Cited

U.S. PATENT DOCUMENTS 6,201,517 B1    3/2001  Sato
6,273,566 B1    8/2001  Kobayashi et al.
(Continued)

FOREIGN PATENT DOCUMENTS

CN      107582237 A     1/2018
CN      107636514 A     1/2018
(Continued)

OTHER PUBLICATIONS

European Search Report dated Mar. 4, 2021, issued in European Application No. 19751204.9.
(Continued)

*Primary Examiner* — Travis S Fissel
(74) *Attorney, Agent, or Firm* — Jefferson IP Law, LLP

(57) ABSTRACT

Accordingly, the embodiments of the disclosure provide a method for determining refractive power of an eye of a wearer. The method includes causing to display, by a first electronic device (100), a virtual image of at least one optotype on a display (202) of a second electronic device (200). Further, the method includes varying, by the first electronic device (100), a focus of the optotypes to provide changes in an optical prescription. Further, the method includes conducting, by the first electronic device (100), an eye exam of the wearer based on the varied focus of the optotypes. Further, the method includes determining, by the
(Continued)

first electronic device (100), the refractive power of the eye of the wearer.

16 Claims, 10 Drawing Sheets

(51) Int. Cl.
*G06V 40/16* (2022.01)
*G06V 40/18* (2022.01)

(58) Field of Classification Search
CPC ............... G06V 40/161; G06V 40/193; G02B 27/0172
USPC .................................................. 351/205–247
See application file for complete search history.

(56) References Cited

U.S. PATENT DOCUMENTS

| | | | |
|---|---|---|---|
| 2009/0153796 A1* | 6/2009 | Rabner | A61B 3/024 351/203 |
| 2017/0000335 A1 | 1/2017 | Samec et al. | |
| 2017/0079523 A1* | 3/2017 | Limon | A61B 3/036 |

FOREIGN PATENT DOCUMENTS

| | | |
|---|---|---|
| EP | 1 928 295 A2 | 6/2008 |
| JP | 2016-172036 A | 9/2016 |
| WO | 2007/026368 A2 | 3/2007 |
| WO | 2011/133945 A1 | 10/2011 |
| WO | 2016/115285 A1 | 7/2016 |
| WO | 2017/061677 A1 | 4/2017 |

OTHER PUBLICATIONS

Richard J. Kolker, MD, Subjective Refraction and Prescribing Glasses, The Number One (or Number Two) Guide to Practical Techniques and Principles, Nov. 2014.
Peek https://www.peekvision.org.
Smarter With Gartner https://www.gartner.com/smarterwithgartner/.
Chinese Office Action dated Sep. 28, 2021, issued in Chinese Application No. 201980012294.0.
Indian Office Action dated Oct. 1, 2021, issued in Indian Application No. 201841004682.
Hearing Notice dated Dec. 29, 2023, issued in Indian Application No. 201841004682.

* cited by examiner

[Fig. 1A]
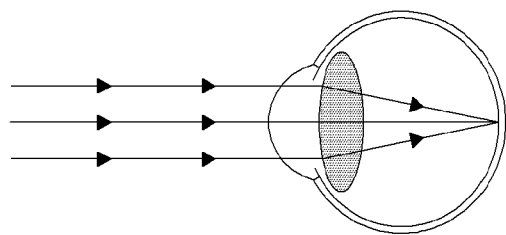
[Fig. 1B]
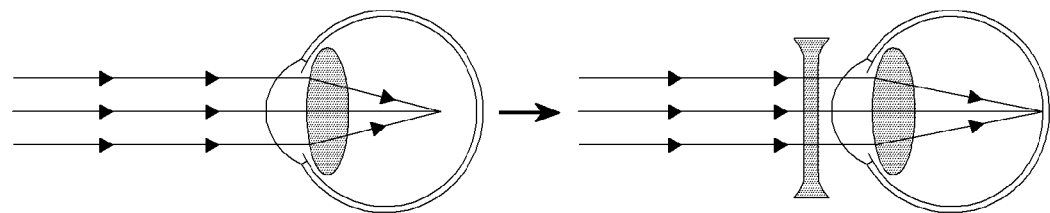
[Fig. 1C]
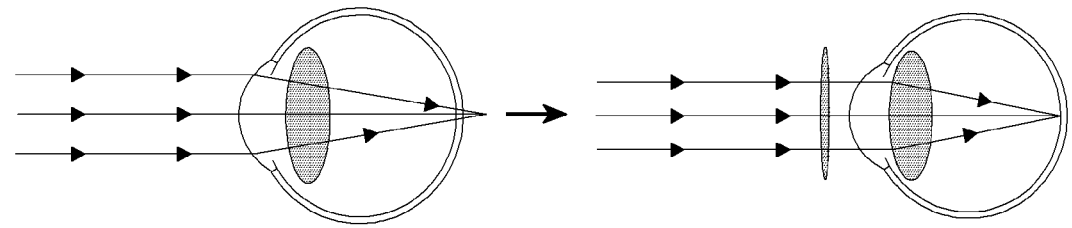

[Fig. 2]
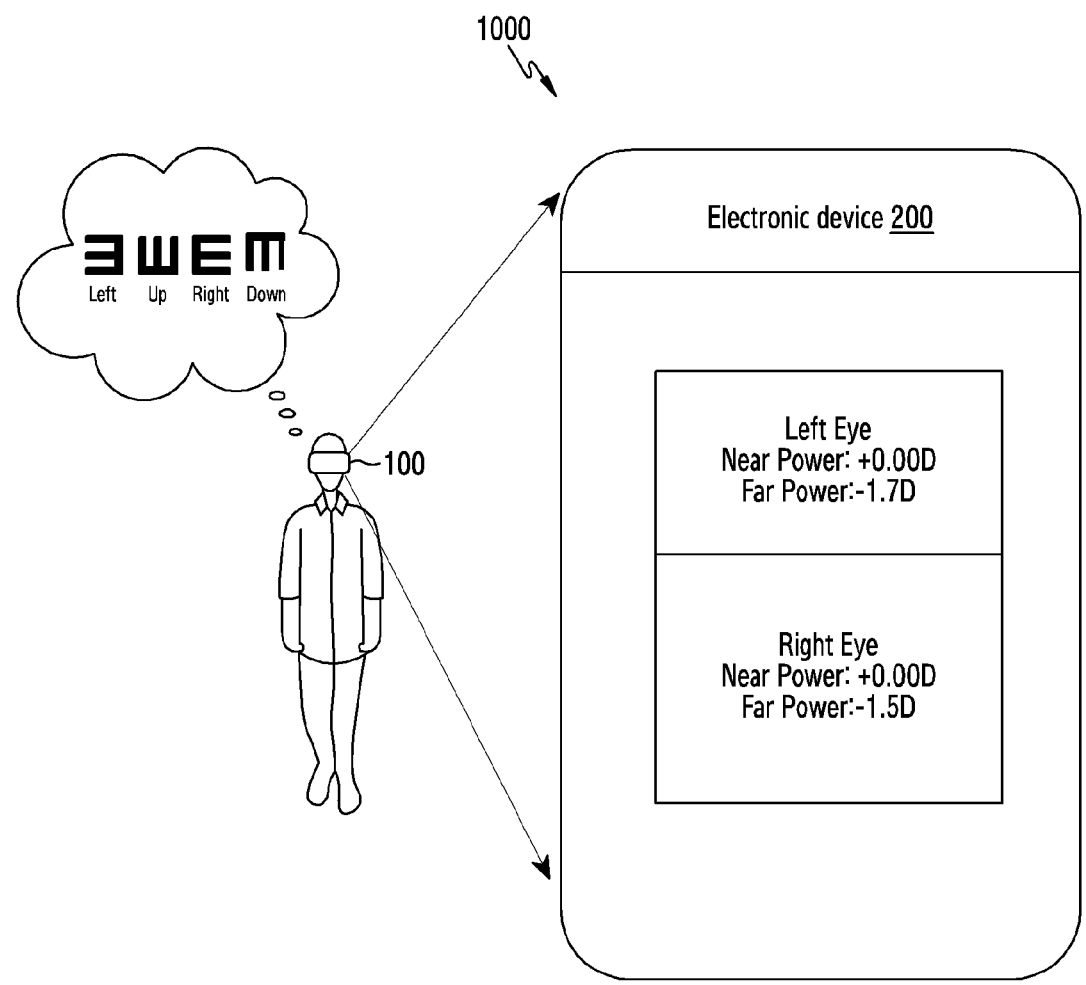

[Fig. 3]
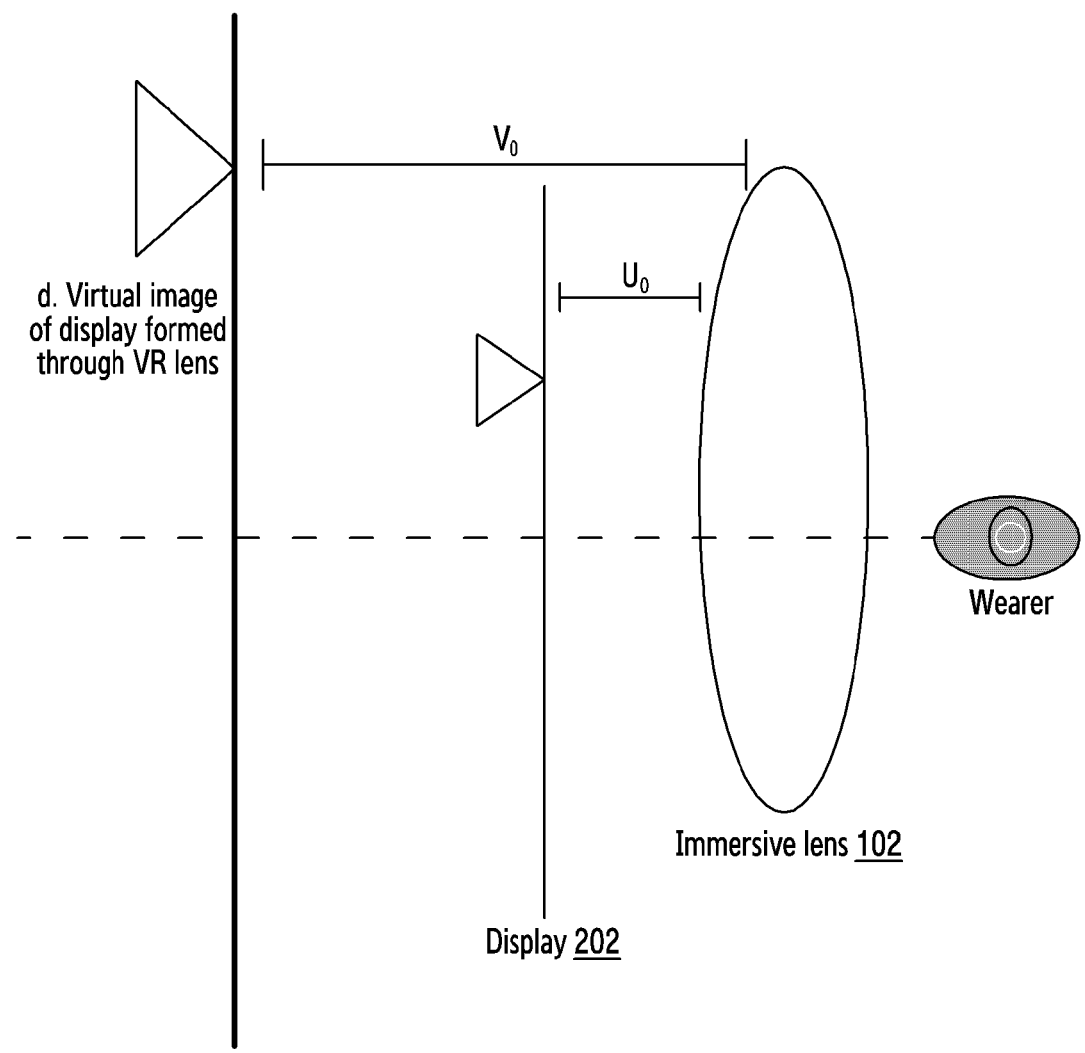

[Fig. 4]
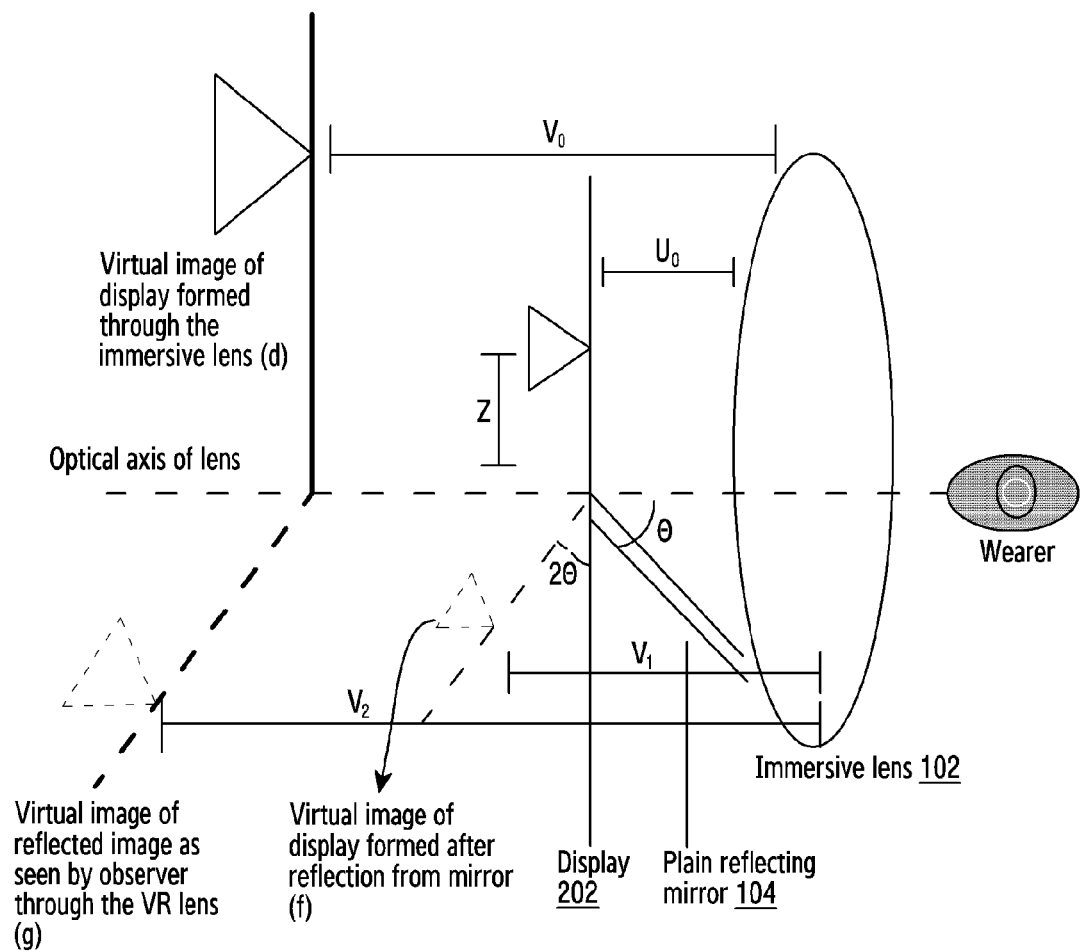

[Fig. 5]
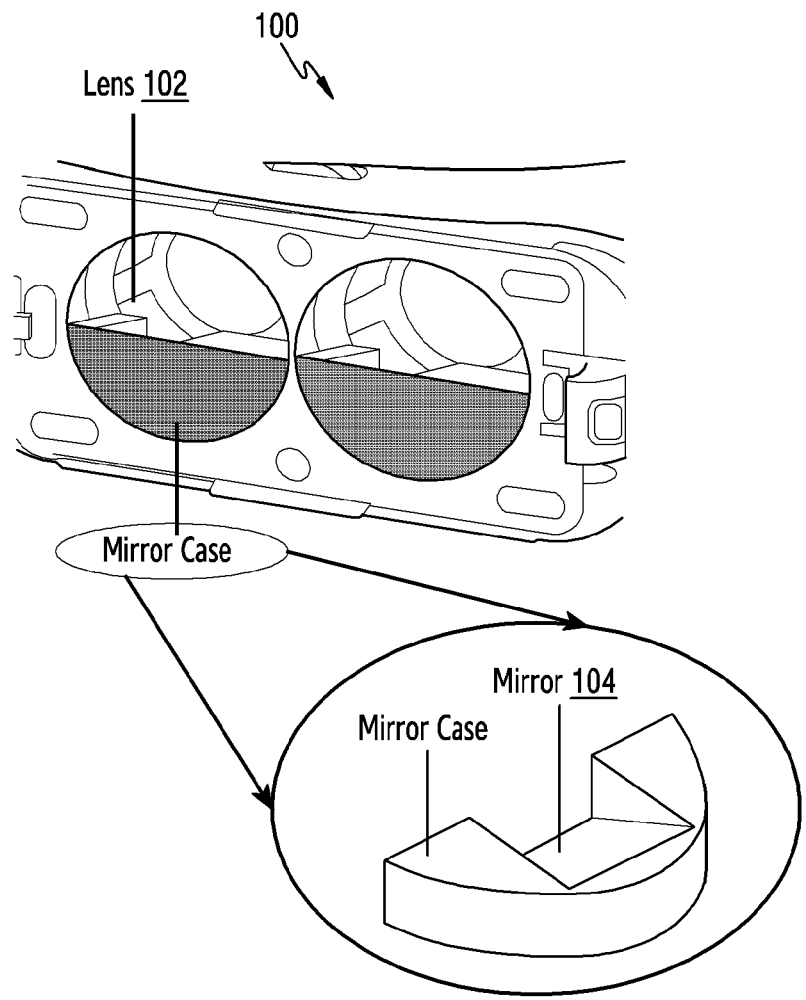
[Fig. 6]
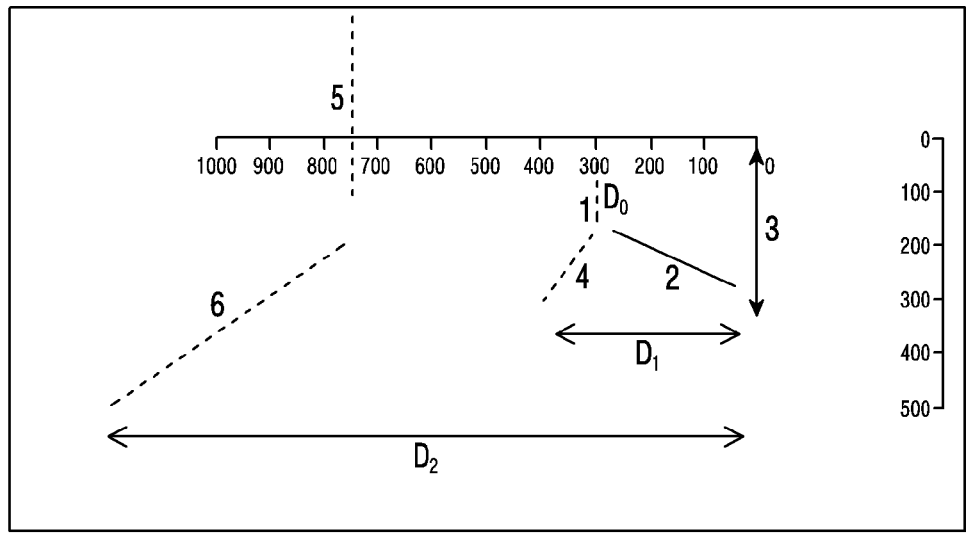

[Fig. 7]
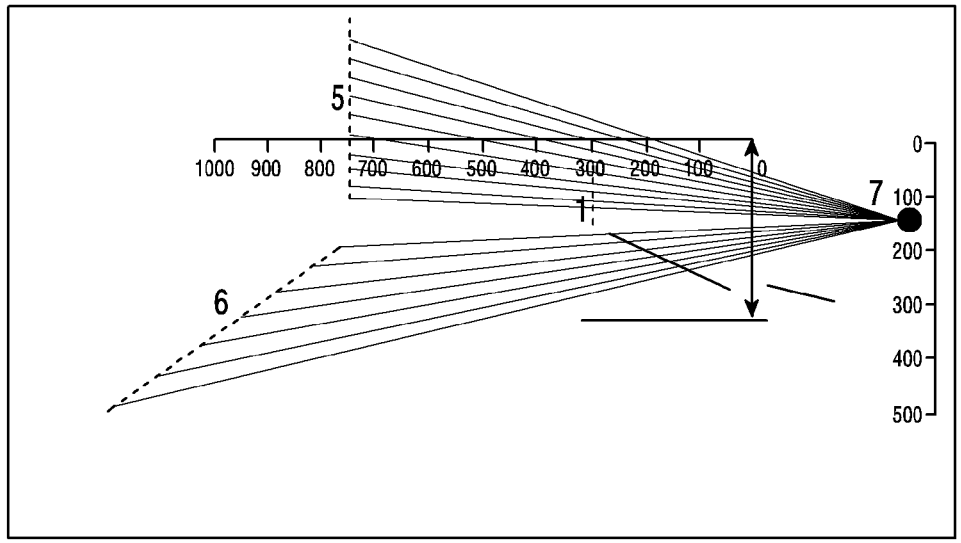
[Fig. 8]
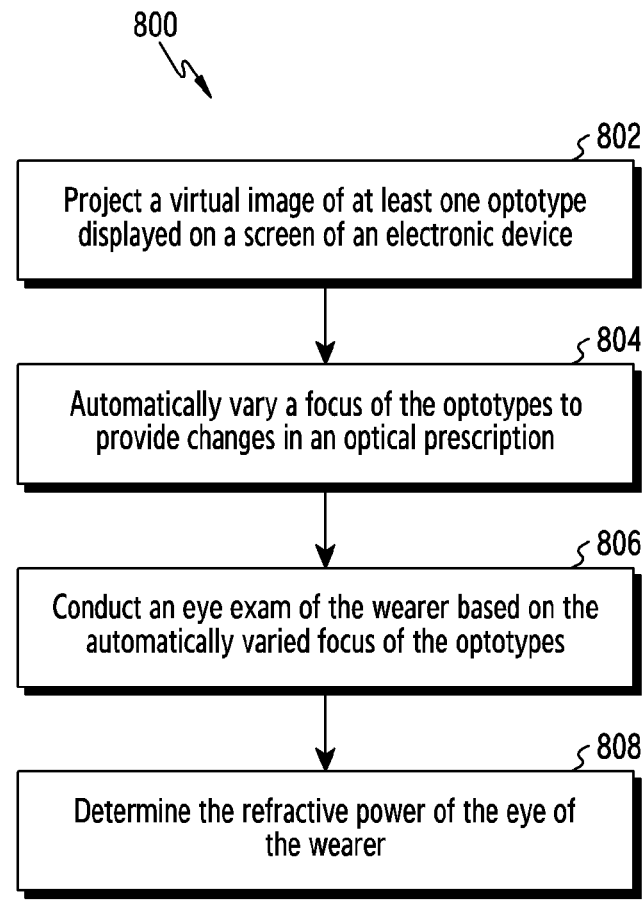

[Fig. 9]
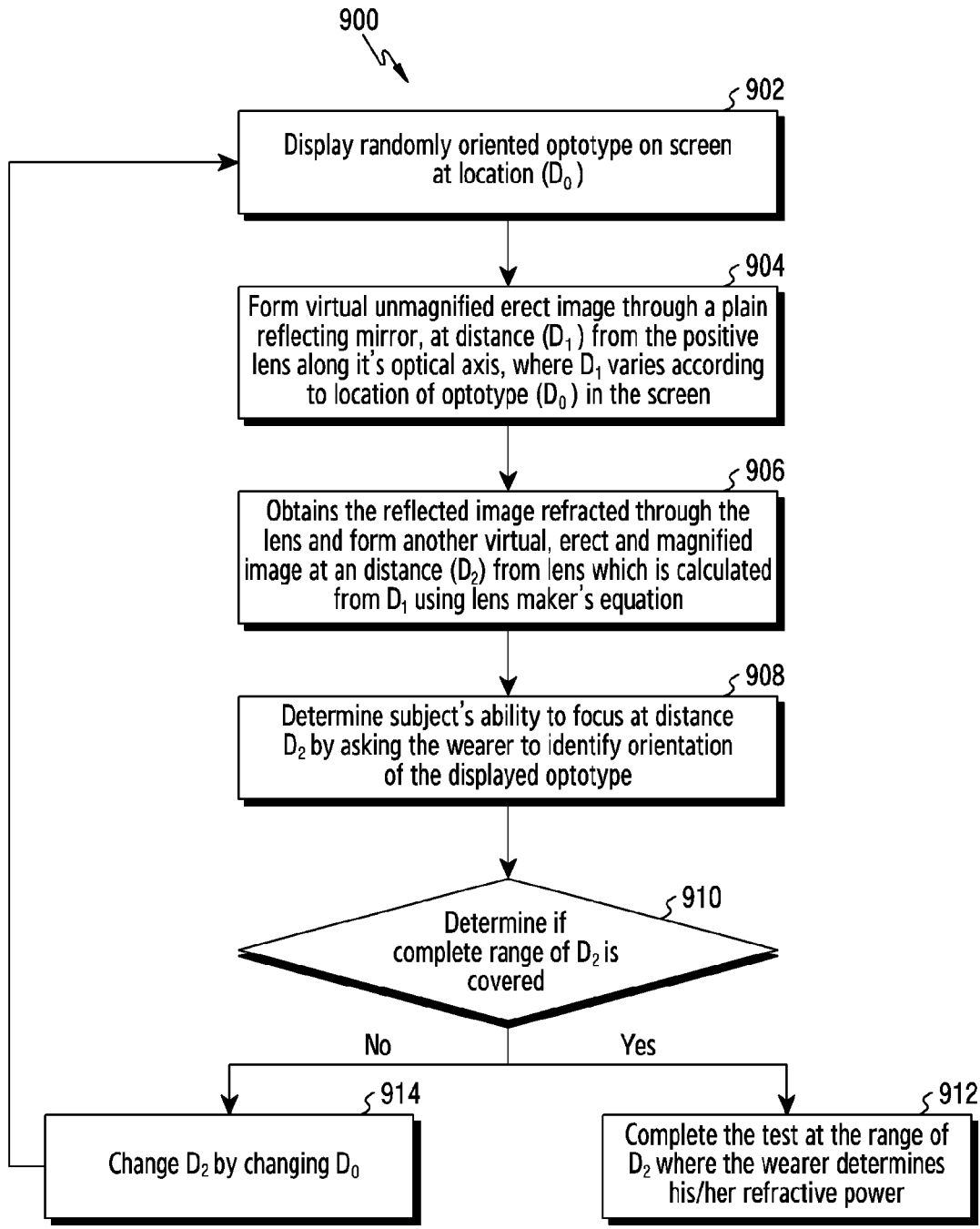

[Fig. 10]
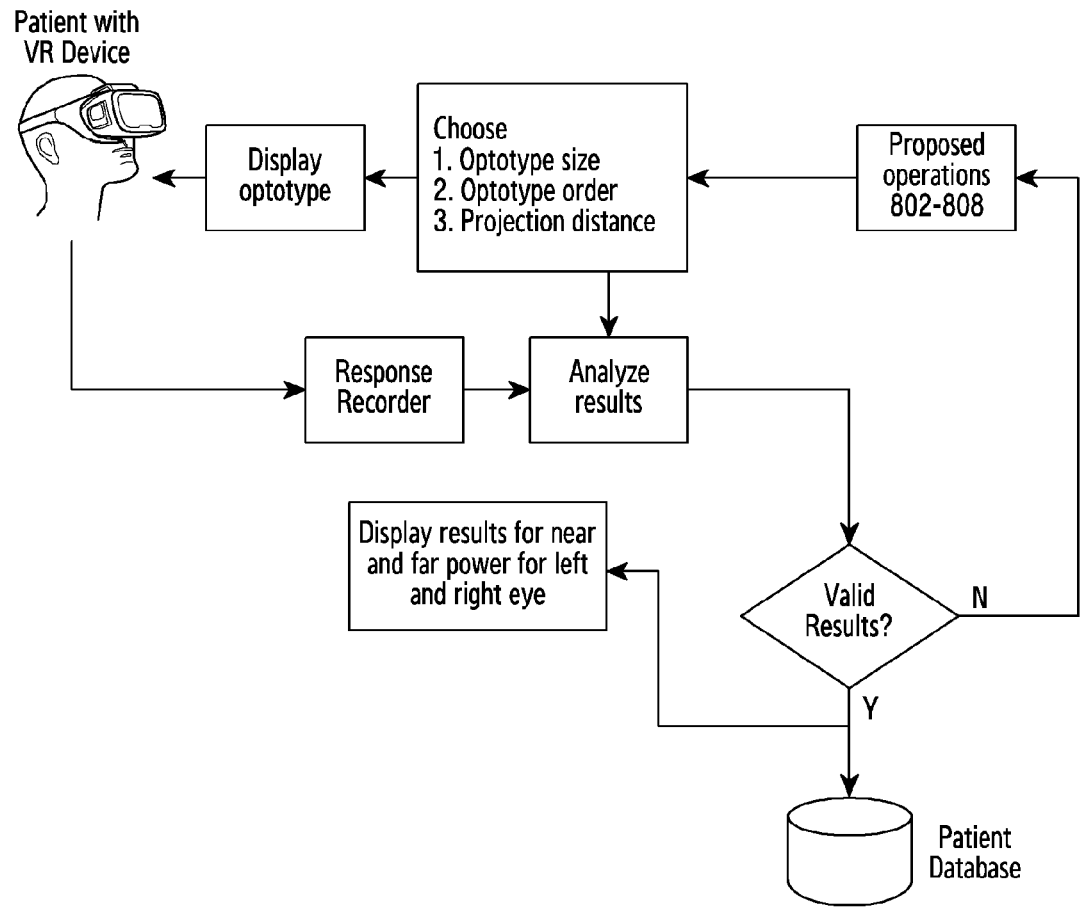
[Fig. 11]
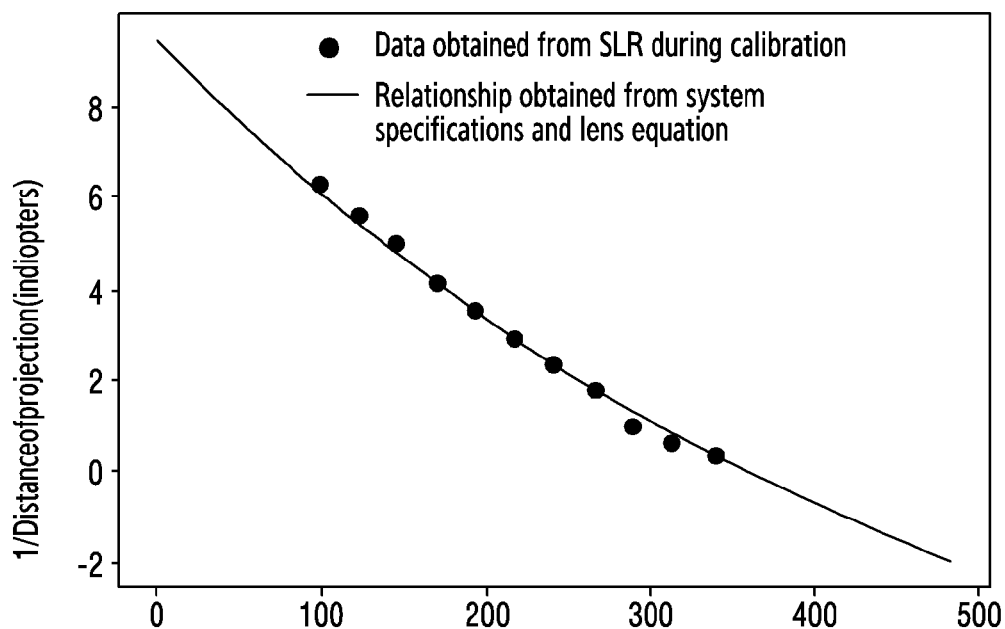

[Fig. 12A]
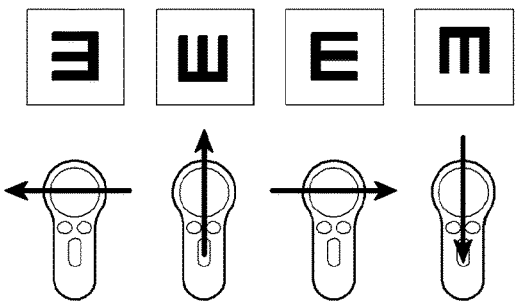
[Fig. 12B]
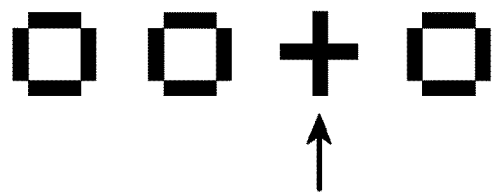
[Fig. 12C]
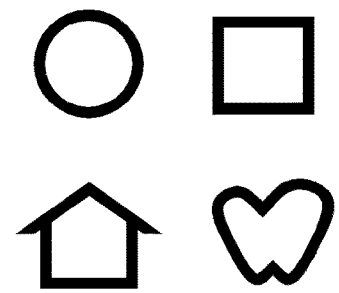
[Fig. 12D]
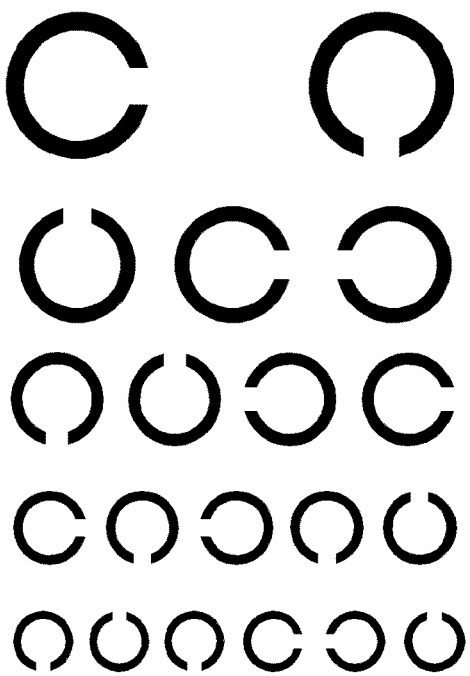

[Fig. 13]
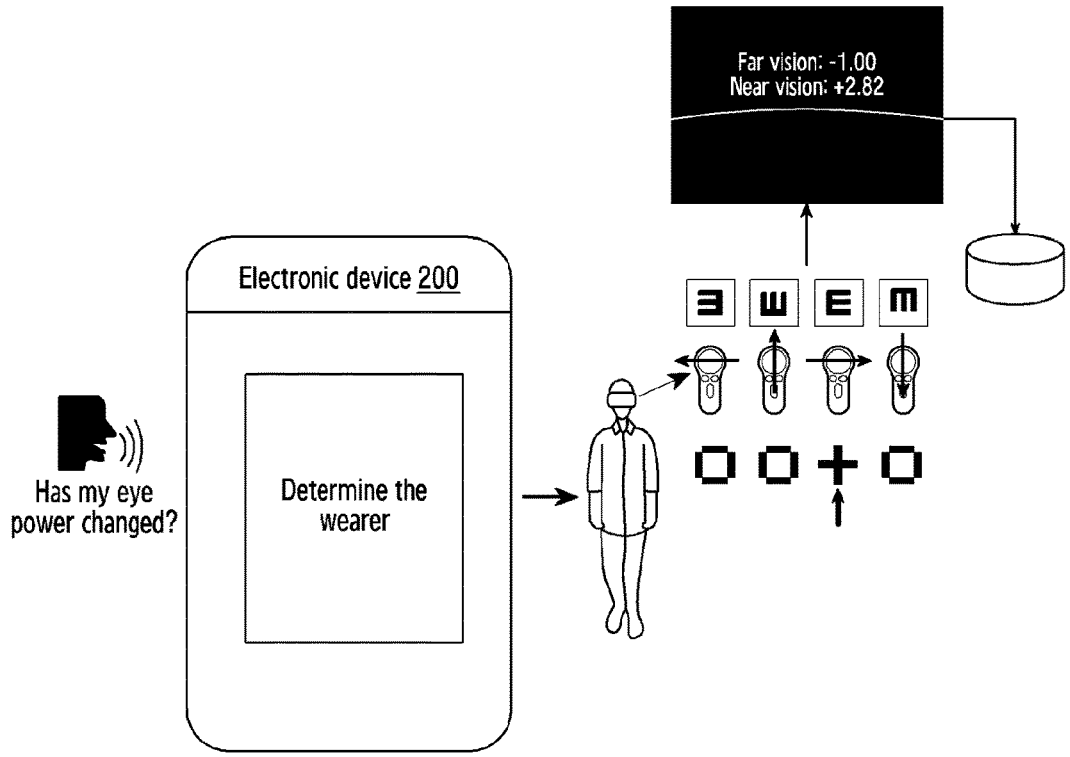
[Fig. 14]
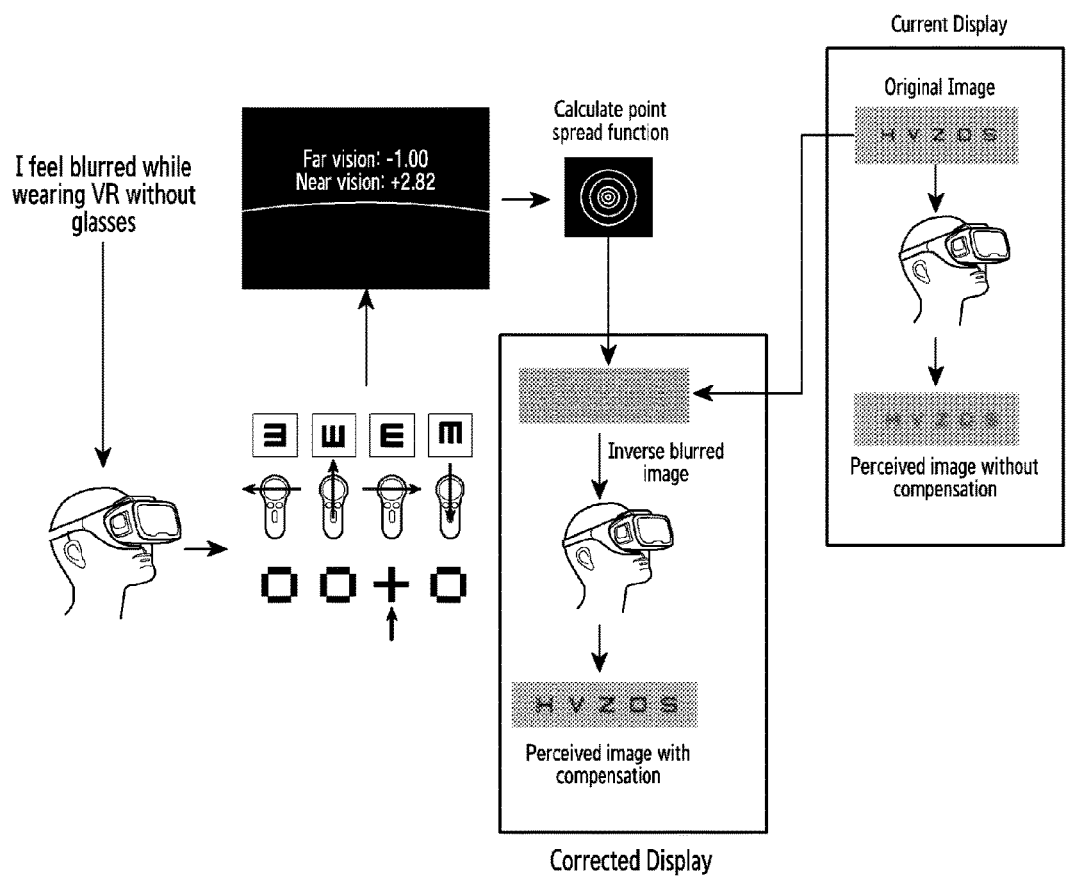

METHOD FOR DETERMINING REFRACTIVE POWER OF EYE USING IMMERSIVE SYSTEM AND ELECTRONIC DEVICE THEREOF

CROSS-REFERENCE TO RELATED APPLICATION(S)

This application is a U.S. National Stage application under 35 U.S.C. § 371 of an International application number PCT/KR2019/001539, filed on Feb. 7, 2019, which is based on and claimed priority of an Indian patent application number 201841004682, filed on Feb. 7, 2018, in the Indian Intellectual Property Office, and of an Indian patent application number 201841004682, filed on Feb. 4, 2019, in the Indian Intellectual Property Office, the disclosure of each of which is incorporated by reference herein in its entirety.

TECHNICAL FIELD

The disclosure relates to an immersive system, and more specifically related to a method and system for estimating a refractive power of an eye using the immersive system.

BACKGROUND ART

A human eye is a complex camera-type imaging system, where objects at wide ranging distances are dynamically focused onto, retina, a photo-sensitive tissue. This dynamic focus is possible due to an adjustable refractive power of the eye, originating from the combination of a cornea and a crystalline lens. The cornea provides a fixed refractive power (i.e., approximately two-thirds of the eye's total focusing power). The crystalline lens can however change its shape to focus the objects at various distances onto the retina. This resulting in adjustable optical power of the eye. This adaptation of the lens shape is known as accommodation, and the range of distances where the eye can focus is called accommodation range.

Defects in the shape of the eyeball, cornea or the lens cause difficulty or inability to focus the light properly onto the retina, such defects are called refractive errors and the symptoms may include blurred vision, double vision, headaches and eye-strain. FIG. 1A-FIG. 1C illustrate common types of the refractive disorders of the human eye, their consequences and corrections.

As shown in the FIG. 1A, a fully relaxed eye focuses rays originating from infinity sharply on the retina resulting in perfect vision, and this condition is called as Emmetropia. As shown in the FIG. 1B, the rays originating from infinity are focused in front of retina. This resulting in far objects appearing blurred while close up objects are sharp. This condition is commonly known as nearsightedness or Myopia. The Myopia can be corrected using concave (negative) lens. As shown in the FIG. 1C, the rays originating from infinity are focused beyond retina. In this condition, far objects appear clear while close up objects are blurry. This condition is commonly known as farsightedness or Hyperopia. Hyperopia can be corrected using a convex lens (i.e., positive lens). Additionally, presbyopia is a condition where accommodation range of the eye is compromised, resulting in both close-up and distant objects appearing blurred. Other refractive disorders include astigmatism and higher order errors, caused by irregular shape of the cornea resulting in radially non-symmetric focus.

Further, advancement of electronic device displays and virtual reality headsets has opened new opportunity for remote eye-health care via interactive systems. This results in minimizing dependency on trained specialists and cumbersome clinical setups Currently, for measuring refractive eye power, a person has to visit a clinician/optician where different lenses are tried out to read letters/alphabet at a distance>4 m. There is no easy way to track/monitor progression of eye sight impairment at home on a "demand basis". The user might for instance want to detect his eye power progression at the earliest before visiting a clinician. Further, the user might want to know if there is any change in the existing eye sight using an electronic device (e.g., smart phone).

In the existing methods, the two types of methods for estimating the refractive eye power are an objective method and a subjective method. In the objective method, the method can be used to detect and estimate refractive errors without actively involving the subject. In Retinoscopy, eye's fundus is illuminated and a retinoscope is used to study the light reflex of the pupil and measure the eye's refractive state. Hence, a shape of eye lens measured directly by projecting a reference pattern onto fundus and then either recording reflected retro or aligning an interrogating pattern. Auto-refractors project known light patterns in the subject's eye and measure distortion of the images formed on the retina. Most auto-refractors including the Shack-Hartmann technique are based on Scheiner's principle. Objective methods require specialized optical instruments and trained professionals, limiting their use for remote eye-health care. Sophisticated instruments with moving optical parts for optical axis alignment and controlling accommodation, special wavelength light emitters are involved in the objective method. Supervisions are generally required and instruments rarely available outside a clinical setup.

In the subjective method, a measurement of refractive errors are determined using a feedback from active participation of the subject. The user is asked to read calibrated charts containing standard symbols or optotypes under controlled distances and illumination, read letters or aligning patterns etc. Refractive errors are measured by recording the subject's judgment on sharpness of the eye-chart after wearing various trial lenses. Subjective tests are unsuitable when interaction with the user is not possible, for example young children. Finding corrective prescription of subject's eye is an involved procedure, typically a two-step process. Refractive errors are first estimated using an autorefractor and then refined using subjective procedure. Generally, specialized hardware with moving parts and light emitters and detectors are used in the subjective method. Uses mobile screen instead of specialized and purpose specific light emitters. Emulates a limited light field display using combination of micro lens array and pinholes. No moving optical parts and light detectors required. However optical parts used are not available commercially for other purposes and are specialized for measuring eye refracting power.

The above information is presented as background information only to assist with an understanding of the disclosure. No determination has been made, and no assertion is made, as to whether any of the above might be applicable as prior art with regard to the disclosure.

DISCLOSURE OF INVENTION

Technical Problem

An embodiment of the disclosure is to provide a method and system for determining refractive power of eye using an immersive system.

An embodiment of the disclosure is to display a virtual image of at least one optotype on a display of an electronic device.

An embodiment of the disclosure herein is to vary a focus of the optotypes to provide changes in an optical prescription.

An embodiment of the disclosure herein is to conduct an eye exam of the wearer based on the varied focus of the optotypes Solution to Problem According to an embodiment of the disclosure, a method for determining refractive power of an eye of a wearer is provided. The method includes causing to display, by a first electronic device, a virtual image of at least one optotype on a display of a second electronic device. Further, the method includes varying, by the first electronic device, a focus of the optotypes to provide changes in an optical prescription. Further, the method includes conducting, by the first electronic device, an eye exam of the wearer based on the varied focus of the optotypes. Further, the method includes determining, by the first electronic device, the refractive power of the eye of the wearer.

In an embodiment, the virtual image of the displayed optotypes is formed using a combination of a positive lens present in the first electronic device and a plain reflecting mirror inserted in the first electronic device.

In an embodiment, the virtual image of the at least one optotype is displayed on the display onto variable optical distances.

In an embodiment, the plain reflecting mirror is placed inside the first electronic device, wherein the plain reflecting mirror is placed front of the display of a second electronic device configured to generate a programmable depth perception.

In an embodiment, causing to display, by the first electronic device, the virtual image of the at least one optotype on the display includes randomly projecting the oriented optotype on the display of the second electronic device at first distance, forming a first virtual unmagnified erect image through a plain reflecting mirror at a second distance from a positive lens along an optical axis of the positive lens (i.e., positive immersive lens), wherein the second distance is varied based on the first distance of the oriented optotype, and forming a second virtual unmagnified erect image through the plain reflecting mirror at a third distance, wherein the second virtual unmagnified erect image is reflection of the first virtual unmagnified erect image.

In an embodiment, the virtual image of at least one optotype is displayed on the display of the second electronic device by placing display of the second electronic device close to a user with a converging lens.

In an embodiment, the method further comprises providing, by the first electronic device, a notification to the wearer.

In an embodiment, the refractive power of the eye of the wearer is determined based on a user history, behavior trait, a user preference, user profile information, and a user account.

In an embodiment, the refractive power of the eye of the wearer is determined based on a voice input mechanism, a finger print mechanism, a face recognition mechanism, and an iris recognition mechanism.

In an embodiment, the method further includes storing, by the first electronic device, the refractive power of the eye of the wearer in a memory.

In an embodiment, the refractive power of the eye indicates a spherical refractive disorder, wherein the spherical refractive disorder comprises at least one of a myopia, a hyperopia and a presbyopia.

In an embodiment, the refractive power of the eye provides a suggestion about a corrective spherical lens for the user.

According to an embodiment of the disclosure, a system for determining refractive power of an eye of a wearer is provided. The system includes a second electronic device comprising a display. The display is coupled with a first electronic device. The first electronic device includes a plain reflecting mirror and a positive lens. The first electronic device is configured to display a virtual image of at least one optotype on a display of a second electronic device. The first electronic device is configured to vary a focus of the optotypes for providing changes in an optical prescription. The first electronic device is configured to conduct an eye exam of the wearer based on the varied focus of the optotypes. The first electronic device is configured to determine the refractive power of the eye of the wearer.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

Advantageous Effects of Invention

Various embodiments of the disclosure provide a scheme for estimating a refractive power of an eye more effectively.

BRIEF DESCRIPTION OF DRAWINGS

This method is illustrated in the accompanying drawings, throughout which like reference letters indicate corresponding parts in the various figures. The embodiments herein will be better understood from the following description with reference to the drawings, in which:

FIG. 1A illustrates an example where rays are focused on retina of human eye;

FIG. 1B illustrates an example where rays are focused in front of retina of human eye;

FIG. 1C illustrates an example where rays are focused beyond retina of human eye;

FIG. 2 illustrating an example scenario in which a system estimates spherical refractive errors of a user using an immersive system, according to an embodiment of the disclosure;

FIG. 3 illustrates an overview of an optical setup of a typical VR environment, according to an embodiment of the disclosure;

FIG. 4 illustrates an overview of a proposed optical setup of the VR environment, according to an embodiment of the disclosure;

FIG. 5 is an exploded view of an immersive system, according to an embodiment of the disclosure.

FIG. 6 is an example arrangement in which arrangements and operations of the immersive system is depicted, according to an embodiment of the disclosure;

FIG. 7 illustrates an example scenario in which the exemplary power of the eye is estimated using the immersive system, according to an embodiment of the disclosure;

FIG. 8 illustrates a flow diagram of a method for determining refractive power of the eye of a wearer, according to an embodiment of the disclosure;

FIG. 9 is a flow chart illustrating various operations for projecting the virtual image of the at least one optotype displayed on the display, according to an embodiment of the disclosure;

FIG. 10 illustrates example flow diagram of various operations for determining refractive power of the eye of the wearer, according to an embodiment of the disclosure;

FIG. 11 illustrates a calibration data for verifying the relationship between the projected distance of the displayed object and its vertical coordinate on the display, according to an embodiment of the disclosure;

FIG. 12A is an example scenario in which various optotypes are displayed, according to an embodiment of the disclosure;

FIG. 12B is another example scenario in which various optotypes are displayed, according to an embodiment of the disclosure;

FIG. 12C is further another example scenario in which various optotypes are displayed, according to an embodiment of the disclosure;

FIG. 12D is yet another example scenario in which various optotypes are displayed, according to an embodiment of the disclosure;

FIG. 13 is an example scenarios in which the system determines the refractive power of the eye of the wearer, according to an embodiment of the disclosure; and FIG. 14 is another example scenarios in which the system determines the refractive power of the eye of the wearer, according to an embodiment of the disclosure.

BEST MODE FOR CARRYING OUT THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

As is traditional in the field, embodiments may be described and illustrated in terms of blocks which carry out a described function or functions. These blocks, which may be referred to herein as units or modules or the like, are physically implemented by analog or digital circuits such as logic gates, integrated circuits, microprocessors, microcontrollers, memory circuits, passive electronic components, active electronic components, optical components, hardwired circuits, or the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the invention. Likewise, the blocks of the embodiments may be physically combined into more complex blocks without departing from the scope of the invention The accompanying drawings are used to help easily understand various technical features and it should be understood that the embodiments presented herein are not limited by the accompanying drawings. As such, the disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

The terms, such as "first", "second", and the like used herein may refer to various elements of various embodiments of the disclosure, but do not limit the elements. For example, "a first user device" and "a second user device" may indicate different user devices regardless of the order or priority thereof. For example, "a first user device" and "a second user device" indicate different user devices. For example, without departing the scope of the disclosure, a first element may be referred to as a second element, and similarly, a second element may be referred to as a first element.

According to the situation, the expression "configured to" used herein may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor (AP)) which performs corresponding operations by executing one or more software programs which are stored in a memory device.

The terms "wearer", "user", "viewer", and "subject" are used interchangeably in the disclosure. The terms "display" and "screen" are used interchangeably in the disclosure.

Accordingly, the embodiments herein achieve a method for determining refractive power of an eye of a wearer. The method includes causing to display, by an immersive system, a virtual image of at least one optotype displayed on a display of an electronic device. Further, the method includes varying, by the immersive system, a focus of the optotypes to provide changes in an optical prescription. Further, the method includes conducting, by the immersive system, an eye exam of the wearer based on the varied focus of the optotypes. Further, the method includes determining, by the immersive system, the refractive power of the eye of the wearer.

The method can be used to estimate the refractive power of the eye using the immersive system (e.g., virtual reality (VR) apparatus, augmented reality (AR) apparatus, a mixed AR apparatus or the like) in a simple, cost effective and accurate manner. The method can be used to estimate the human eye's spherical refractive errors without additional hardware elements, without using mechanically moving parts and expert's assistance. The method can be used to receive the feedback from user based on an interaction so as to estimate an accommodation range, spherical refractive errors and a speed of focus automatically in an effective manner.

In an example, the immersive system can be used to assess each eye independently and while one of the eye is being tested, the other eye's view is completely blacked out. The immersive system is configured to display optotypes and record multiple observations to make system robust to guessing. Further, the immersive system displays different symbols (e.g., optotypes or the like) at controlled depths and record user's feedback on perceived clarity of the symbols using a VR controller. In an example, Letter "E" of Tumbling E chart oriented randomly in one of the four directions (such as right direction, up-ward direction, down-ward direction and left direction) is displayed and the user is asked to swipe on the VR controller in corresponding direction (as shown in the FIG. 12A). The user can double tap on the VR controller if the displayed optotype appears blurred and the user is unable to identify its orientation.

For each observation, three types of subject feedback are possible such as correct, incorrect and uncertain response. When the user registers multiple incorrect and/or uncertain response (corresponding to double tap) for a particular distance, the immersive system infers that the user cannot accommodate to that distance and accordingly identify the refractive errors.

The proposed method can be used to minimize a bulkiness of system for estimating refractive power and dependence on specialists.

Unlike conventional methods and systems, the proposed method enables a direct projection of a virtual image of optotypes displayed on an electronic device screen onto variable optical distances, which are controllable through logics without any moving parts. The virtual image of displayed optotypes is formed using a combination of a positive lens (i.e., positive immersive lens or the like) already present in the immersive system and a plain reflecting mirror which can be inserted in the immersive system. This enables reflection based depth simulation to estimate visual acuity, detection of myopia, hyperopia and presbyopia along with automatic refractive power prescription. The primary advantage of the proposed methods is that the wearer can measure their refractive eye power in their home setting. Further, the proposed system will allow to capture earliest eye sight impairment. Further, the user can compare and keep track of their eye sight at frequent intervals.

Further, the proposed method enables the electronic device to use immersive system to estimate refractive power of the eye without demanding more additional hardware requirements. The refractive power is estimated by recording subject's ability to focus at displayed optotype. Individual optotypes can be projected at varying optical distances.

The method can be used to provide refraction test results to arrive at prescription for spherical refractive errors correction in a cost effective manner. The method can be used to detect refractive disorders and identifies myopia, hyperopia and presbyopia. The method can be used to determine uncorrected and best corrected visual acuity by changing size of optotypes. The method can be used to detect range of distances at which user can focus (i.e., accommodation range). The method can be used to measure speed of accommodation. The method allows the users to take breaks anytime during the test to avoid eye fatigue. In the proposed methods, an optical system in the immersive system projects the display patterns (e.g., optotypes or the like) at programmable controlled distances from the eye.

The method can be used to automatically predict and track onset and progression of visual refractive disorders based on a longitudinal test data. This is based on data stored in cloud/analytics platform of the proposed system. The method can be used to estimate the refractive power of the eye using the immersive system in a quick manner by eliminating time delays caused by manually changing lenses.

The variety of display patterns and optotypes are designed to remove dependency on ability of user to read any language or script. The method can be used to estimate the refractive power of the eye using the immersive system in a customized manner based on the user data. The method can be used improve the visual experience for users who want to wear VR headset without glasses.

Referring now to the drawings, and more particularly to FIGS. 2-14, where similar reference characters denote corresponding features consistently throughout the figures, there are shown exemplary embodiments.

FIG. 2 illustrating an example scenario in which the system 1000 estimates spherical refractive errors of a user using an immersive system 100, according to an embodiment of the disclosure. In an embodiment, the system 1000 includes the immersive system 100 and an electronic device 200. The immersive system 100 can be, for example, but not limited to, a VR apparatus, an AR apparatus, a mixed AR apparatus, a head mounted display, a subjective refractive power measurement apparatus or the like. The electronic device 200 can be, for example, but not limited to, a smart phone, a mobile phone, a tablet, a smart glass or the like. The electronic device 200 includes a display (not shown), where the display is coupled with the immersive system 100. The immersive system 100 includes a plain reflecting mirror (not shown) and a positive lens (not shown). The immersive system 100 is configured to project a virtual image of at least one optotype displayed on a screen (not shown) of the electronic device 200. The immersive system 100 and the electronic device 200 may be implemented as a single device and may be referred as an electronic device. The immersive system 100 and the electronic device 200 may be implemented as different devices, and may be referred a first electronic device and a second electronic device, respectively.

In an example, the user sees the pixels displayed on the immersive system 100 through the positive lens during an eye exam. Any image formed through the positive lens can either be real or virtual. In the proposed system 1000, the image as seen by the user is virtual. For example, if a letter "E", oriented to the right is displayed on the smart phone, the same is seen by the user.

In the proposed system 1000, the eye exam is similar to a clinical subjective refraction test. In a clinical setup, trial lenses are put on physically and then the user is asked to read the eye charts, whereas, in the proposed system 1000, the eye exam emulates the clinical setup inside a VR environment. Objectives of the eye exam are to determine user's eye health and provide optical prescription.

In an embodiment, the virtual image of the at least one optotype is projected on the screen by randomly projecting the oriented optotype on the screen of the electronic device 200 at first distance, forming a first virtual unmagnified erect image through the plain reflecting mirror at a second distance from the positive lens along an optical axis of the positive lens, wherein the second distance is varied based on the first distance of the oriented optotype, and forming a second virtual unmagnified erect image through the plain reflecting mirror at a third distance, wherein the second virtual unmagnified erect image is reflection of the first virtual unmagnified erect image.

In an embodiment, the virtual image of at least one optotype is displayed on the screen of the electronic device by placing display of the electronic device close to a user with a converging lens.

Further, the immersive system 100 is configured to vary a focus of the optotypes for providing changes in an optical prescription. Based on the varied focus of the optotypes, the immersive system 100 is configured to conduct the eye exam of the wearer. The immersive system 100 is configured to determine the refractive power of the eye of the wearer based on the eye exam.

The optical prescription is defined as the set of specifications of the corrective spherical lens needed for each eye to restore normal vision. The optical prescription may change over time. In an example, the optical prescriptions for the myopic user in left eye is −0.5 Distance and right eye is −1.0 Distance and the optical prescriptions for the hyperopia user in left eye is +0.75 Distance and right eye is +1.5 Distance. The various operations for projecting the virtual image of the at least one optotype displayed on the display and varying the focus of the optotypes to provide changes in the optical prescription are explained in conjunction with the FIG. 9 and FIG. 10.

In an example, the user wants to check his/her eye power. The user wears the immersive system 100 and the immersive system 100 selects the optotype size, orientation/order and projection distance based on user's past data if any past data is present or defaults to a preset value. The optotype is displayed and the projection depth as decided by the proposed system 1000 is set using flow described in the FIG. 9. Further, the user registers his/her response, depending upon whether he/she can see the optotype clearly or not. This process is repeated with different projection distances. At each distance, the immersive system 100 has recorded the response of the user. This data of user's response and projection distance is used by proposed method to compute the corrective optical prescription for the user during the myopic test. Similar steps can be extended for a hyperopia test and a presbyopia test.

In an embodiment, the refractive power of the eye of the wearer is determined based on a user data (e.g., user history, behavior trait, a user preference, user profile information, a user account or the like).

In an embodiment, the refractive power of the eye of the wearer is determined based on a voice input mechanism, a finger print mechanism, a face recognition mechanism, and an iris recognition mechanism. In an embodiment, the refractive power of the eye indicates a spherical refractive disorder, wherein the spherical refractive disorder comprises at least one of a myopia, a hyperopia and a presbyopia.

In an embodiment, the refractive power of the eye provides a suggestion about a corrective spherical lens for the user.

In an example, the user data (e.g., user history, behavior trait, a user preference, user profile information, and a user account or the like) are needed to progressively track eye health of the user over time. Further, the biometric information (e.g., voice input mechanism, finger print mechanism, face recognition mechanism, iris recognition mechanism or the like) is used for user identification and authentication. Consider, the user informs to the immersive system 100 that "Please check if my eye power has changed". Based on the query, the immersive system 100 will then prompt user to identify himself/herself using biometrics as access to sensitive health data is restricted to the particular user only. Once authentication and identification is complete, the immersive system 100 can retrieve past data of the user containing results of previously conducted eye tests. This allows the immersive system 100 to intelligently control the projection depths instead of using preset values. The preset values are used when no past data is available. Intelligent control reduces total examination time and errors.

In an embodiment, the virtual image of the displayed optotypes is formed using a combination of the positive lens present in the immersive system 100 and the plain reflecting mirror inserted in the immersive system 100. In an embodiment, the virtual image of the at least one optotype is displayed on the screen onto variable optical distances.

In an embodiment, the plain reflecting mirror is placed inside the immersive system 100, wherein the plain reflecting mirror is placed front of the display of the electronic device 200 configured to generate a programmable depth perception. In the disclosures, varying optical distances and generating programmable depth perception refer to the same thing as depth and optical distance both are here referred to the projected distance of the optotype as seen by the user.

In an embodiment, the immersive system 100 is configured to provide a notification to the wearer. In an embodiment, the immersive system 100 is configured to store the refractive power of the eye of the wearer in a memory (not shown).

The user wears the immersive system 100 normally and interacts with a logic through an immersive controller (not shown). The depth at which objects are projected through the logic is controllable and hence a focus range of the user's eyes can determine. The logic corresponds to control the projected depth of final image of the optotype as seen by the user by the display. Further, changing the pixel location of the displayed optotype changing projected depth of the final image of the optotype as seen by the user is controlled by the logic.

Unlike conventional systems, the proposed system 1000 is used to estimate refractive errors in a VR environment or an AR environment by reusing commercially available hardware of the immersive system 100 and the electronic device 200. The system 1000 enables users to determine their spherical refractive errors by simply interacting with the logic in the VR environment or an AR environment. The immersive system 100 enables projection of displayed objects at constrained programmable distances from the user's eye, without expensive, sophisticated or moving optical parts. Further the system 1000 includes an interactive procedure which simulates the clinical setup consisting of trial lenses, eye charts and ophthalmologist in a VR environment or an AR environment allowing remote measurement of refractive errors. The interactive procedure are explained in the FIG. 8 to FIG. 10.

Further, the immersive system includes a memory (not shown) also stores instructions to be executed by the processor (not shown). The memory may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory may, in some examples, be considered a non-transitory storage medium. The term "non-transitory" may indicate that the storage medium is not embodied in a carrier wave or a propagated signal. However, the term "non-transitory" should not be interpreted that the memory is non-movable. In some examples, the memory can be configured to store larger amounts of information than the memory. In certain examples, a non-transitory storage medium may store data that can, over time, change (e.g., in Random Access Memory (RAM) or cache).

In an embodiment, the immersive system 100 includes a virtual image projecting unit, an optotypes focus varying unit, an eye exam conducting unit used for determining the refractive power of the eye of the wearer.

Although the FIG. 2 shows various hardware components of the system 1000 but it is to be understood that other embodiments are not limited thereon. In other embodiments, the system 1000 may include less or more number of components. Further, the labels or names of the components are used only for illustrative purpose and does not limit the scope of the invention. One or more components can be combined together to perform same or substantially similar function to determine the refractive power of the eye of the wearer.

FIG. 3 illustrates an overview of an optical setup of the typical VR environment, according to an embodiment of the disclosure. The display 202 is held very close to the user (i.e., observer) with the immersive lens 102 (i.e., converging lens) such that the display 202 is closer to the lens than its focal point, so as to create a magnified and virtual image. The focal length of the lens to be f and its distance from the display to be $u_0$. The virtual image is formed at a distance $v_0$ from the lens, given by the thin lens formula, Equation 1:

$$\frac{1}{v_0} = \frac{1}{u_0} - \frac{1}{f} \qquad \text{Equation 1}$$

Here f is positive and $u_0<f$.

FIG. 4 illustrates an overview of the proposed optical setup of the VR environment, according to an embodiment of the disclosure. The plain reelecting mirror 104 (i.e., tilted mirror) is introduced between the display 202 and the lens 102 such that a reflecting side of the lens 102 is facing the observer. The reflected image of the display 202 is depicted by the gray dashed line and pointer (f). The virtual image of this reflected image is seen by the observer $v_2$ through the lens 102, represented by black dashed line and pointer (g). Consider, the mirror 104 is tilted at an angle of θ radians from optical axis of the lens and this axis is normal to the display plane. It follows from the laws of reflection that the display 202 and its reflected image subtend equal angles at the mirror, i.e. $(\pi/2)+\theta$. Therefore, acute angle between the display and its reflected image is 2θ. Consider a pixel on the display 202 at a distance z from its top, as indicated by the marker. Its reflection in the mirror 104, as depicted by the gray dashed marker, is at a distance v1=u0+z sin (2θ) from the lens 102 along its optical axis. When seen through the lens 102, virtual image of this reflection is formed at a distance v2 given by Equation 2:

$$\frac{1}{v_2} = \frac{1}{u_1} - \frac{1}{f} = \frac{1}{u_0 + z\sin(2\theta)} - \frac{1}{f} \qquad \text{Equation 2}$$

By changing the pixel location on the display 202, the distance between focal plane of the pixel can vary as seen by the observer and his/her eyes. Therefore, using the plane reflecting mirror 104, the proposed system 1000 achieves projection of displayed objects at constrained programmable distances from the observer.

FIG. 5 is an exploded view of the immersive system 100, according to an embodiment of the disclosure. As shown in the FIG. 5, the display 202 is held very close to the user with the immersive lens 102. Further, the plain reflecting mirror 104 is arranged between the display 202 and the immersive lens 102 such that a reflecting side of the immersive lens 102 is facing the user, such that the geometrical optics creates the programmable depth perception.

FIG. 6 is an example arrangement in which arrangements and operations of the immersive system 100 is depicted, according to an embodiment of the disclosure. In the immersive system 100, Part-1 represents the display 202 attached to a VR headset. Part-2 represents a plain reflecting mirror 104 inserted in the VR headset. Part-3 represents a positive lens 102 already present inside the VR headset. Part-4 represents a virtual unmagnified image of the displayed objects in part-1 through a mirror reflection part. Part-5 represents a magnified image of displayed objects in part-1 through a lens refraction part. Part-6 represents a magnified image of reflected virtual image in the part-4 through a lens refraction. This magnified image is used for refractive power assessment.

FIG. 7 illustrates an example scenario in which the refractive power of the eye is estimated using the immersive system 100, according to an embodiment of the disclosure. The FIG. 7 is a ray diagram illustrating optics in the FIG. 6.

FIG. 8 illustrates a flow diagram 800 of a method for determining refractive power of the eye of the wearer, according to an embodiment of the disclosure. The operations (802-808) are performed by the immersive system 100. At 802, the method includes projecting the virtual image of at least one optotype displayed on the display 202 of the electronic device 200. At 804, the method includes automatically varying the focus of the optotypes to provide changes in the optical prescription. At 806, the method includes conducting the eye exam of the wearer based on the automatically varied focus of the optotypes. At 808, the method includes determining the refractive power of the eye of the wearer.

The various actions, acts, blocks, steps, or the like in the flow diagram 800 may be performed in the order presented, in a different order or simultaneously. Further, in some embodiments, some of the actions, acts, blocks, steps, or the like may be omitted, added, modified, skipped, or the like without departing from the scope of the invention.

FIG. 9 is a flow chart 900 illustrating various operations for projecting the virtual image of the at least one optotype displayed on the screen 202, according to an embodiment of the disclosure. The operations (902-914) are performed by the immersive system 100.

At 902, the method includes displaying randomly oriented optotype on the screen 202 at location (Do). At 904, the method includes forming the virtual unmagnified erect image through the plain reflecting mirror 104, at distance $(D_1)$ from the positive lens 102 along it's optical axis. $D_1$ varies according to location of optotype $(D_0)$ in the screen 202. At 906, the method includes obtaining the reflected image refracted through the lens and forming another virtual, erect and magnified image at a distance $(D_2)$ from the lens 102 which is calculated from $D_1$ using lens maker's equation. At 908, the method includes determining wearer's ability to focus at distance $D_2$ by asking the wearer to identify orientation of the displayed optotype. At 910, the method includes determining if complete range of $D_2$ is covered. If complete range of $D_2$ is covered then, at 912, the method includes complete the test at the range of $D_2$ where the wearer determines his/her refractive power. If complete range of $D_2$ is not covered then, at 914, the method includes changing $D_2$ by changing $D_0$.

The various actions, acts, blocks, steps, or the like in the flow diagram 900 may be performed in the order presented, in a different order or simultaneously. Further, in some embodiments, some of the actions, acts, blocks, steps, or the like may be omitted, added, modified, skipped, or the like without departing from the scope of the invention.

FIG. 10 illustrates example flow diagram of various operations for determining refractive power of the eye of the wearer, according to an embodiment of the disclosure. The procedure for varying the optical distances is explained in conjunction with the FIG. 4 and FIG. 9. In an example, the user wants to check his/her eye power. The user wears the immersive system 100 and the immersive system 100 selects the optotype size, orientation/order and projection distance based on user's past data if any past data is present or defaults to a preset value. The optotype is displayed and the projection depth as decided by the proposed system 1000 is set using flow described in the FIG. 9. Further, the user registers his/her response, depending upon whether he/she can see the optotype clearly or not. This process is repeated with different projection distances. At each distance, the immersive system 100 has recorded the response of the user. This data of user's response and projection distance is used by proposed method to compute the corrective optical prescription for the user during the myopic test. Similar steps can be extended for a hyperopia test and a presbyopia test.

FIG. 11 illustrates a calibration data for verifying the relationship between the projected distance of the displayed object and its vertical coordinate on the display, according to an embodiment of the disclosure. Equation 2 relates depth of a pixel perceived by the observer ($v_2$) to the pixel's coordinates on the display (z) and system design parameters focal length of the lens, distance between the display and the lens (u0), angle of inclination of the mirror ($\theta$).

The focal length is obtained from the immersive system manufacturer's specifications and $\theta$ can be controlled while designing the setup. Moreover, z is a function of pixel pitch (inverse of pixel density) and pixel coordinates. However, the focal length f and the angle of inclination $\theta$ are subject to manufacturing imprecisions and $u_0$ is generally adjustable. Therefore, it is important to verify the system parameters by optically calibrating the setup.

According to the proposed method, grid like patterns are displayed at different values of z and found the projected distance of the pattern by manually focusing on it using a single-lens reflex (SLR) camera kept near the immersive system 100. Consider, the specified focal length for the immersive system 100 is 50 mm (20 D) and pixel-pitch of display of a mobile phone is 4.46×10$^{-5}$ m. Further, the mirror 104 is inclined to $\theta$=15 degree from optical axis of the lens 102. Further, the screen 202 is adjusted to lens distance at 34 cm. Using these values in Equation 2 inverse of projected distance is obtained as a function of displayed object's vertical coordinate in pixels. Data obtained during calibration process agree with this function, as shown in the FIG. 11.

Equation 2 can be used to find the nearest and furthest of distances at which the proposed system 1000 can project, along with its precision. In order to find the range of the proposed system 1000, the system 1000 can be used to determine the minimum and the maximum of $1/v_2$ in Equation 2 subject to constraints of system parameters. Let the Equation 3:

$$\frac{1}{v_2} = \frac{1}{0.034 + 4.46 \times 10^{-5} y \sin(30°)} - \frac{1}{0.050} \quad \text{Equation 3}$$

Where y=z/μ is vertical coordinate of the displayed object in pixels and μ is the pixel pitch. The display screen resolution is 2960×1440. Due to the mirror placed in front of the display, only half of the total screen is usable. Thus the range of y is (0,720) pixels and consequently, the range of $1/v_2$ is (−4.8, 9.4) diopters. However, aforementioned theoretical range cannot be utilized completely due to the thickness of the reflecting mirror 104 and the limits of field of view in the immersive system 100. Precision $\Delta 1/v_2$ can be calculated by Equation 4:

$$\Delta\left(\frac{1}{v_2}\right) = \quad \text{Equation 4}$$

$$\left|\frac{\partial v_2}{\partial y}\right| \cdot \Delta y \leq \max\left\{\left|\frac{-\mu \sin(2\theta)}{(u_0 + \mu y \sin(2\theta))^2}\right|\right\} \cdot \Delta y \leq \left|\frac{\mu \sin(2\theta)}{u_0^2}\right| \cdot \Delta y$$

Here, $\Delta y$ is the minimum possible change in pixel coordinate, trivially 1. Therefore, precision of inverse of depth projection is 1.93×10$^{-4}$ diopters. It is noteworthy that precision of prescription glasses is generally 0.25 diopters.

FIG. 12A-FIG. 12D are example scenarios in which various optotypes are displayed, according to an embodiment of the disclosure. As shown in the FIG. 12A-FIG. 12D, consider a scenario, optotypes are displayed in the tumbling E chart and a corresponding expected response are explained here. As shown in Equation 2, perceived depth of a pixel can be controlled precisely by varying its coordinates on the display 202. By exploiting this phenomenon, the trial lens and eye-chart setup inside the immersive system 100 is simulated. The different symbols (optotypes) at controlled depths and record subject's feedback on perceived clarity of these optotypes are displayed using a Gear VR controller. Registering subject's feedback on conventional charts (e.g., Snellen, log MAR or the like) using a typical VR controller is difficult owing to limited number of controls offered by these input methods. Therefore, adaptation of two types of charts is employed in the proposed method.

Display Patterns—Optotypes:

In an example, tumbling E chart: Letter "E" oriented randomly at one of the four directions—right, up, down and left is displayed and the user is asked to swipe on the controller in corresponding direction. Additionally, the user can double tap on the controller if the displayed optotype appears blurred and the user is unable to identify its orientation. Arrows superimposed on the Gear VR controller depict the swipe direction for a particular optotype.

Rendering Optotypes:

It is noteworthy that although magnification factor of each pixel depends upon its vertical coordinate, wearer can only perceive the angle subtended by an object on their eyes. This angle depends on the ratio of image dimensions and distance from the eye. However, image magnification increases linearly with its distance from the lens. Moreover, even though distance of an image from the eye is sum of its distance from the lens 102 and eye to lens separation, the VR lens 102 are generally held very close to the eye and lens 102 to eye separation distance can be ignored. Therefore, independent of its location and consequently the projected depth, every pixel appears to be of approximately the same size.

As evident from FIG. 4, due to reflection from the inclined mirror 104, the final image as seen by observer through the lens is tilted. When the object of finite size is displayed, vertical angle subtended on the observer's eye by the object shrinks by a factor of cos (2×) while horizontal angle remains unchanged, creating a distortion. Here x is angle of inclination of the mirror with respect to the optical axis of the lens 102. In order to overcome this distortion, the system 1000 elongates the displayed objects by a factor of 1/cos (2×) along their vertical dimension.

Estimating Accommodation Range:

A single pass procedure is employed to estimate accommodation range of the user. Each eye is assessed independently and while one of the eye is being tested, the other eye's view is completely blacked out. The optotypes are displayed, at projected distances from $D_{min}$ to $\infty$, where $D_{min}=12.5$ cm is the minimum possible projection distance. Following rules are followed to estimate near and far point:

Near Point: Starting from Dmin, i.e. the minimum distance at which the system 1000 can project, hence gradually move the projection further and find the nearest distance at which the user registers all correct responses and denote it as his/her near point.

Far Point: Starting from ∞, gradually move the projection closer and find the furthest distance at which all of the subject's responses are correct and mark it as his/her far point.

Suggestive Refractive Error Correction:

Finding corrective prescription of subject's eye is an involved procedure, where an eye doctor analyzes results of objective and subjective refraction and uses his/her judgment to arrive at prescription. However, similar to autorefractors, the proposed system 1000 can be used to provide indicative optical refractive power for near and far vision. Although the system 1000 is validated on myopia subjects, it can be easily extended to test hyperopia and presbyopia using following procedure:

Myopia:

Optical refractive power of the lens 102 required to correct blurry far vision can be inferred directly from the subject's far point. Assuming the far point is $d_{far}$, it follows from the lens equation that the corrective refractive power needed to help the subject focus at optical infinity is $P_{far}=-1/d_{far}$.

Hyperopia:

Starting from $D_{max}$, i.e. the furthest distance beyond infinity at which the system 1000 can project (negative since beyond infinity), gradually move the projection plane towards infinity until the subject registers all correct responses at some distance, say $d_{hyp}$. The plus spherical corrective refractive power is calculated as $P_{hyp}=-1/d_{hyp}$ ($d_{hyp}$ is negative since beyond infinity). This is equivalent to finding maximum plus spherical power the subject can tolerate without causing blurring or discomfort while reading an eye chart 20 feet away.

Presbyopia:

When both near and far vision become blurred, separate spherical correction refractive power is required for each. Far blurred vision is corrected using negative spherical refractive power calculated exactly as in the case of myopia. However, near refractive power is corrected using positive spherical refractive power, calculated using the near point of the subject. Consider, the near point of the subject by $d_{near}$ and ideal near point by $d_{ideal}$. It is noteworthy that although we use 35 cm as ideal near point, it is subjective and depends on ideal reading distance of every subject. The plus refractive power is calculated as $P_{near}=1/d_{ideal}-1/d_{near}$. Trivially, no near vision correction is needed if $d_{near} \leq d_{ideal}$.

FIG. 13 and FIG. 14 are example scenarios in which system 1000 determines the refractive power of the eye of the wearer, according to an embodiment of the disclosure. As shown in the FIG. 13, the user recently started wearing glasses and wants to track his/her eye power frequently without visiting clinic. Based on the proposed methods, the person wears the VR device and interacts with a game-like logic to take the eye test personalized for him/her using his/her past data.

As shown in the FIG. 14, the person wears the VR device and takes the eye test. The results for both eyes are used for spherical aberration compensatory rendering of VR display improving his/her visual experience and reducing discomfort.

The embodiments disclosed herein can be implemented through at least one software program running on at least one hardware device and performing network management functions to control the elements.

The foregoing description of the specific embodiments will so fully reveal the general nature of the embodiments herein that others can, by applying current knowledge, readily modify and or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of exemplary preferred embodiments, those skilled in the art will recognize that the embodiments herein can be practiced with modification within the spirit and scope of the embodiments as described herein.

The invention claimed is:

1. A method for determining a refractive power of an eye of a wearer, the method being performed by an immersive system and comprising:
    causing to display, through a positive lens, at least one optotype on a display of the immersive system;
    changing a focus of the at least one optotype reflected using a plane reflecting mirror by changing a location of the at least one optotype on the display, such that a projection distance of the at least one optotype as seen by the wearer is changed;
    obtaining a response about the changed focus of the at least one optotype as seen by the wearer; and
    determining the refractive power of the eye of the wearer based on the response and the projection distance,
    wherein the immersive system comprises the positive lens and the plane reflecting mirror disposed separately from the display, and
    wherein the plane reflecting mirror is at an angle to an optical axis of the positive lens, and the optical axis is normal to the display.

2. The method of claim 1, wherein the at least one optotype is formed using a combination of the positive lens of the immersive system and the plane reflecting mirror inserted in the immersive system.

3. The method of claim 1, wherein the at least one optotype is displayed on the display onto variable optical distances.

4. The method of claim 2,
wherein the plane reflecting mirror is disposed inside the immersive system, and
wherein the plane reflecting mirror is located in front of the display and configured to generate variable optical distances.

5. The method of claim 1, wherein the causing to display the at least one optotype on the display comprises:
randomly projecting the at least one optotype on the display of a second electronic device at first distance;
forming a first virtual unmagnified erect image through the plane reflecting mirror at a second distance from the positive lens along the optical axis of the positive lens, wherein the second distance is changed based on the first distance of an oriented optotype;
forming a second virtual unmagnified erect image through the plane reflecting mirror at a third distance, wherein the second virtual unmagnified erect image is a reflection of the first virtual unmagnified erect image; and
causing to display the virtual image of the at least one optotype on the display.

6. The method of claim 1, wherein the causing to display the at least one optotype on the display comprises:
placing the display close to the eye of the wearer with the positive lens; and
causing to display the at least one optotype on the display onto variable optical distances.

7. The method of claim 1, further comprising:
providing a notification to the wearer.

8. The method of claim 1, wherein the refractive power of the eye of the wearer is determined based on at least one of a user history, a behavior trait, a user preference, user profile information, or a user account.

9. The method of claim 1, wherein the refractive power of the eye of the wearer is determined in response to identifying and authenticating the wearer based on at least one of a voice input mechanism, a finger print mechanism, a face recognition mechanism, or an iris recognition mechanism.

10. The method of claim 1, further comprising:
storing, in a memory, the refractive power of the eye of the wearer.

11. The method of claim 1,
wherein the refractive power of the eye indicates a spherical refractive disorder, and
wherein the spherical refractive disorder comprises at least one of a myopia, a hyperopia, or a presbyopia.

12. The method of claim 1, wherein the refractive power of the eye provides a suggestion about a corrective spherical lens for the wearer.

13. A system for determining a refractive power of an eye of a wearer, the system comprising:
a first electronic device; and
a second electronic device comprising a display coupled with the first electronic device,
wherein the first electronic device includes a plane reflecting mirror and a positive lens,
wherein the first electronic device is configured to:
display, through the positive lens, at least one optotype on the display of the second electronic device;
change a focus of the at least one optotype reflected using the plane reflecting mirror by changing a location of the at least one optotype on the display, such that a projection distance of the at least one optotype as seen by the wearer is changed;
obtain a response about the changed focus of the at least one optotype as seen by the wearer; and
determine the refractive power of the eye of the wearer based on the response and the projection distance,
wherein the positive lens and the plane reflecting mirror are disposed separately from the second electronic device, and
wherein the plane reflecting mirror is at an angle to an optical axis of the positive lens, and the optical axis is normal to the display.

14. The system of claim 13, wherein the at least one optotype is formed using a combination of the positive lens and the plane reflecting mirror.

15. The system of claim 13, wherein the at least one optotype is displayed on the display onto variable optical distances.

16. The system of claim 13,
wherein the first electronic device comprises at least one of a virtual reality (VR) apparatus, an augmented reality (AR) apparatus, a mixed AR apparatus, a head mounted display, or a subjective refractive power measurement apparatus, and
wherein the second electronic device comprises at least one of a smart phone, a mobile phone, a tablet, or a smart glass.

* * * * *